(12) United States Patent  
Bergman

(10) Patent No.: US 8,826,740 B2  
(45) Date of Patent: Sep. 9, 2014

(54) METHODS AND APPARATUS FOR POROSITY MEASUREMENT AND DEFECT DETECTION

(75) Inventor: Robert William Bergman, Scotia, NY (US)

(73) Assignee: General Electric Company, Schenectady, NY (US)

( * ) Notice: Subject to any disclaimer, the term of this patent is extended or adjusted under 35 U.S.C. 154(b) by 336 days.

(21) Appl. No.: 13/196,314

(22) Filed: Aug. 2, 2011

(65) Prior Publication Data

US 2013/0031979 A1 Feb. 7, 2013

(51) Int. Cl.
*G01N 29/04* (2006.01)
*G01N 29/11* (2006.01)

(52) U.S. Cl.
CPC ........ *G01N 29/11* (2013.01); *G01N 2291/0231* (2013.01); *G01N 29/043* (2013.01); *G01N 2291/0289* (2013.01)
USPC .............................................. 73/602; 73/628

(58) Field of Classification Search
USPC ................................... 73/602, 627, 628, 629
See application file for complete search history.

(56) References Cited

U.S. PATENT DOCUMENTS

| | | | | |
|---|---|---|---|---|
| 7,389,693 | B2 * | 6/2008 | Reed et al. | 73/629 |
| 7,617,730 | B2 * | 11/2009 | Georgeson | 73/602 |
| 7,757,558 | B2 * | 7/2010 | Bossi et al. | 73/609 |
| 2002/0066318 | A1 | 6/2002 | Dubois et al. | |
| 2007/0051177 | A1 | 3/2007 | Gifford et al. | |
| 2007/0095141 | A1 | 5/2007 | Puckett | |
| 2007/0119256 | A1 | 5/2007 | Vaccaro et al. | |
| 2007/0186655 | A1 | 8/2007 | Reed et al. | |
| 2008/0148854 | A1 | 6/2008 | Georgeson et al. | |
| 2008/0229834 | A1 | 9/2008 | Bossi et al. | |

OTHER PUBLICATIONS

Search Report for corresponding EP Application No. 12177765.0 dated Nov. 14, 2012.
Guo, N. et al., "The non-destructive assessment of porosity in composite repairs", vol. 25, No. 9, pp. 842-850, Oct. 1, 1994.
Wu, Ruiming et al., "Modeling of Digital Spectrum Based Ultrasonic Attenuation about Void Content in CFRP", pp. 459-462, Dec. 20, 2008.

* cited by examiner

*Primary Examiner* — John Chapman, Jr.

(74) *Attorney, Agent, or Firm* — James McGinness, Esq.; Armstrong Teasdale LLP

(57) ABSTRACT

A method and apparatus for non-destructively inspecting a composite structure with an ultrasonic system including an ultrasonic probe includes positioning the composite structure in a tank-less environment, and scanning the composite structure with the ultrasonic system to measure ultrasonic sound waves reflected by the composite structure to the single ultrasonic probe. A physical characteristic of the composite structure is determined based at least in part on the measured ultrasonic sound waves.

15 Claims, 8 Drawing Sheets

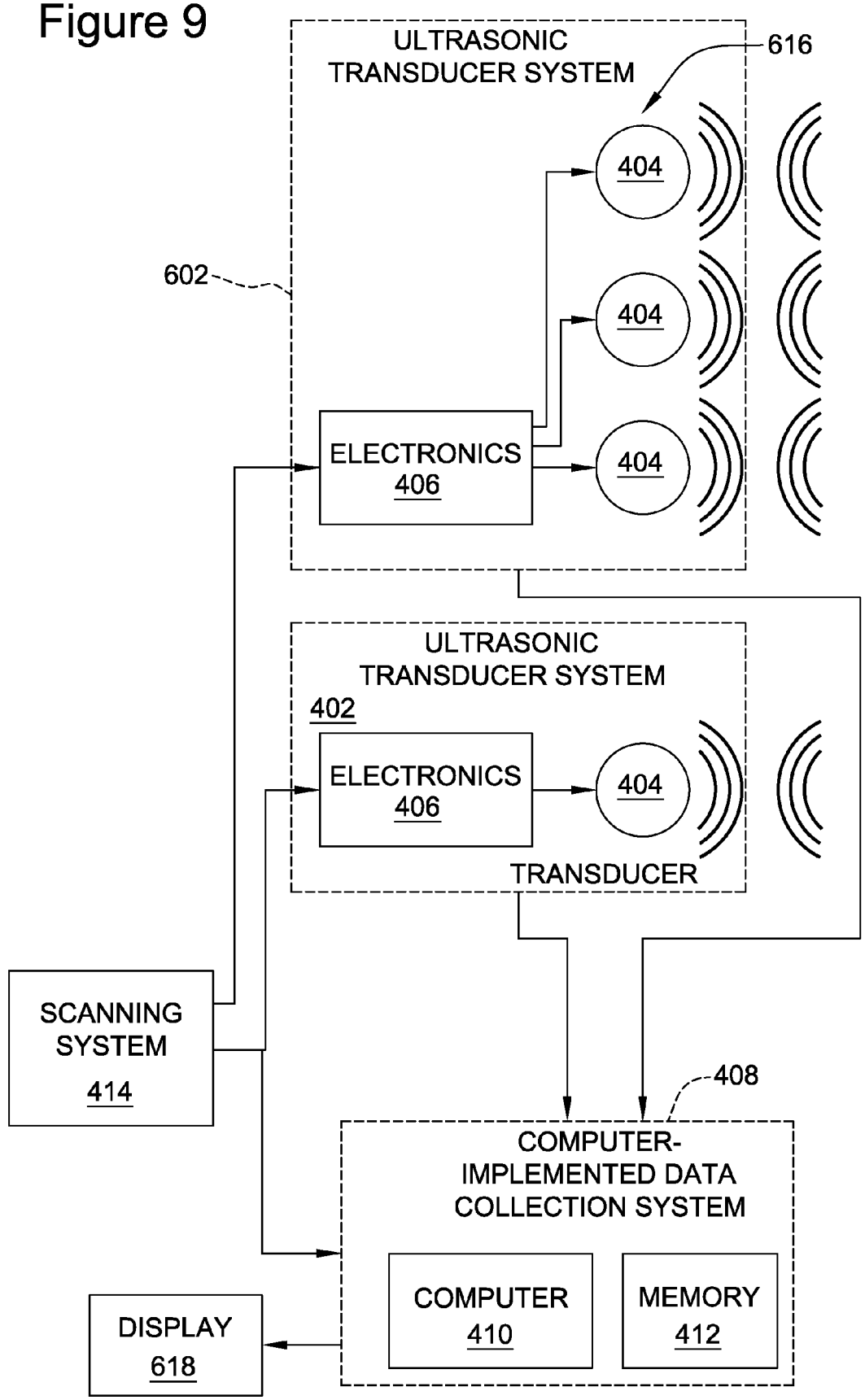

METHODS AND APPARATUS FOR POROSITY MEASUREMENT AND DEFECT DETECTION

BACKGROUND OF THE INVENTION

This invention relates generally to methods and apparatus for nondestructively measuring porosity and detecting defects in composite structures.

New product designs and manufacturing methods of structures based on polymer matrix composites are becoming more prevalent. However, composite structures may have an unacceptable level of volumetric porosity and undetected porosity and defects can lead to early failure of components.

One known method for measuring porosity in composite structures is the use of acid digestion. With acid digestion, the weight percent of matrix material and fiber material are measured separately by using acid to dissolve one of the constituents. Using these data plus mass density information for the separate materials, the percent porosity can easily be determined. However, acid digestion methods are destructive because the composite must be dissolved to measure the volume of porosity. Acid digestion is valuable as a process control tool where either entire parts or sections of parts can be sacrificed to measure the capability of the manufacturing process. For some components, however, this destructive testing method is inadequate since actual structures should be measured.

Some known methods for measuring porosity in composite structures made of fiberglass are based on the observation that pores in a composite structure cause a frequency shift in sound traveling through the structure. These known methods use multiple ultrasonic transducers to measure through transmission through a composite article in an immersion tank to determine sound attenuation to estimate the porosity content in composites. In general, these known methods require precision scanning of two transducers in an immersion tank collecting data at a plurality of frequencies. To collect the ultrasonic information needed to analyze porosity would require two or more scans of the part depending on the attenuation slope calculation method used, a serious limitation to manufacturing productivity. Additionally, two transducers are required for these measurements with their positioning axes. However, most immersion tanks designed for such inspection have only one transducer manipulator.

Another known method for measuring porosity of composite structures made of resin infused fiberglass uses a single transducer to determine sound attenuation by the composite structure in an immersion tank. In this method, sound reflected off the front wall of a composite structure in an immersion tank is compared with sound reflected off the back wall the immersion tank after passing through the composite structure. This known method typically uses a 2.25 MHz frequency transducer.

When composite structures are made of materials other than fiberglass, some of the known methods are not as efficacious. When composite structures are very large, testing the large structure in existing immersion tanks according to the known methods may be impractical or impossible.

BRIEF DESCRIPTION OF THE INVENTION

In one aspect, the present invention provides a method for non-destructively inspecting a composite structure with an ultrasonic system including an ultrasonic probe. The method includes positioning the composite structure in a tank-less environment. The method includes scanning the composite structure with the ultrasonic system to measure ultrasonic sound waves reflected by the composite structure to the single ultrasonic probe. The method includes determining a physical characteristic of the composite structure based at least in part on the measured ultrasonic sound waves.

In yet another aspect, the present invention provides an apparatus for non-destructively inspecting a composite structure. The apparatus has an ultrasonic system including an ultrasonic probe configured to transmit and receive ultrasonic sound waves and electronic equipment configured to operate the ultrasonic transducer to generate and amplify the ultrasonic sound waves. The apparatus includes a data collection system including a computer. The data collection system is configured to collect ultrasonic information. The apparatus is configured to scan a composite structure with the ultrasonic system to measure ultrasonic sound waves reflected by the composite structure to the ultrasonic probe, and determine a physical characteristic of the composite structure based at least in part on the measured ultrasonic sound waves.

In another aspect, the present invention provides a method for non-destructively inspecting a composite structure with an ultrasonic system including an ultrasonic transducer. The method includes calibrating the ultrasonic system on a standard, and scanning a composite structure using a single frequency of sound waves less than about 2 MHz emitted by the ultrasonic transducer to measure an ultrasonic amplitude and a frequency for sound waves reflected by the composite structure to the ultrasonic transducer. The method includes utilizing the measured ultrasonic amplitude to determine an attenuation for sound waves reflected by the composite structure, and determining a porosity percentage for the composite structure as a function of the determined attenuation and the measured frequency.

BRIEF DESCRIPTION OF THE DRAWINGS

FIG. 9 is a block diagram of an inspection system including a single ultrasonic transducer and a phased array probe suitable for use with configurations of the present invention.

DETAILED DESCRIPTION OF THE INVENTION

Figure 1:
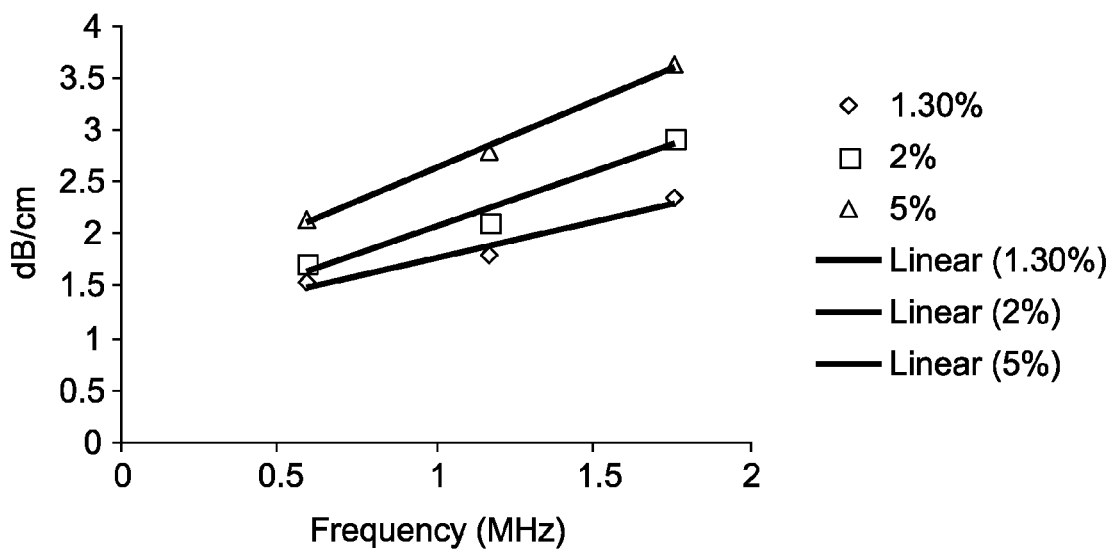
FIG. 1 is a graph plotting measured ultrasonic attenuation by three samples of known porosity as a function of the frequency of the reflected ultrasonic sound waves.

Technical effects of the present invention include the non-destructive measurement of porosity of a composite structure, the non-destructive detection of defects of the composite structure, and/or the generation of a digital image showing cross-sectional physical characteristics of the composite structure.

Unlike some known methods and systems for porosity determination, configurations of the present disclosure do not use an immersion tank and do not use through transmission of sound waves. Tank-less porosity measurement configurations of the present disclosure measure attenuation of the sound waves reflected back from a composite structure at which the sound waves were directed.

Porosity content of a composite structure has an effect on frequency of a sound wave as the sound travels through the composite structure. Higher frequencies generally attenuate faster as sound travels through a material, resulting in a downward shift of the peak frequency of a sound wave passing through the material. In a highly attenuative material, such as a carbon fiber composite structure, it may be beneficial to separate the attenuation of a sound wave due to scatter from the attenuation due to porosity. This can be accomplished because porosity is typically less than one wavelength in diameter whereas other scatter modes are typically greater than one wavelength in size. Scatter mechanisms greater than one wavelength in size work to either absorb or deflect energy whereas porosity less than one wavelength will work to attenuate higher frequencies and shift the returned beam frequency down. Thus, for a given ultrasonic frequency, a composite structure with a greater porosity will produce a greater attenuation of the ultrasonic sound waves. Similarly, a composite structure with a given porosity will produce greater attenuation of higher frequency ultrasonic sound waves than lower frequency ultrasonic sound waves.

Determining the attenuation of a material can be very difficult. In some embodiments, an ultrasonic system including an ultrasonic transducer is first calibrated with a standard of a known attenuation. The standard should typically have characteristics similar to the composite structure to be inspected. An acrylic glass standard, such as polymethyl methacrylate (PMMA) for example, has approximately the same acoustic velocity as carbon fiber composites and is highly attenuative, as are carbon fiber composites. Accordingly, in some embodiments, an acrylic glass standard of a known attenuation is used to calibrate the ultrasonic transducer prior to inspecting a carbon fiber composite structure. In other embodiments, a section of the actual production part to be inspected is used for ultrasonic calibration. The production process for composite structures often results in end products whose acoustic properties vary greatly, causing analysis to be difficult. By using the actual production material to calibrate the ultrasonic transducer, the variation may be significantly mitigated.

FIG. 1 graphically presents the results of ultrasonic inspection of three composite structures using the calibration with a known standard described above. Each composite structure had a known porosity determined by the acid digestion method. The composite structures were carbon fiber composite structures having porosities of 1.3%, 2% and 5%. Each structure was scanned three times, each time using a different transducer. Specifically, the three transducers were a 0.5 MHz transducer, a 1 MHz transducer, and a 2.25 MHz transducer. The standard was a one inch thick piece of acrylic glass.

FIG. 1 plots the attenuation of each composite structure acquired using this method as a function of the frequency of the reflected sound wave. The relationship between attenuation and frequency for a composite structure is a natural logarithmic relationship. This relationship may be approximated, however, by a linear fit. As can be seen in FIG. 1, when approximated by a linear fit, the porosity content of a composite will affect the slope of the line representing the frequency of the ultrasonic beam. Specifically, the greater the porosity, the greater the slope of the line.

Figure 2:
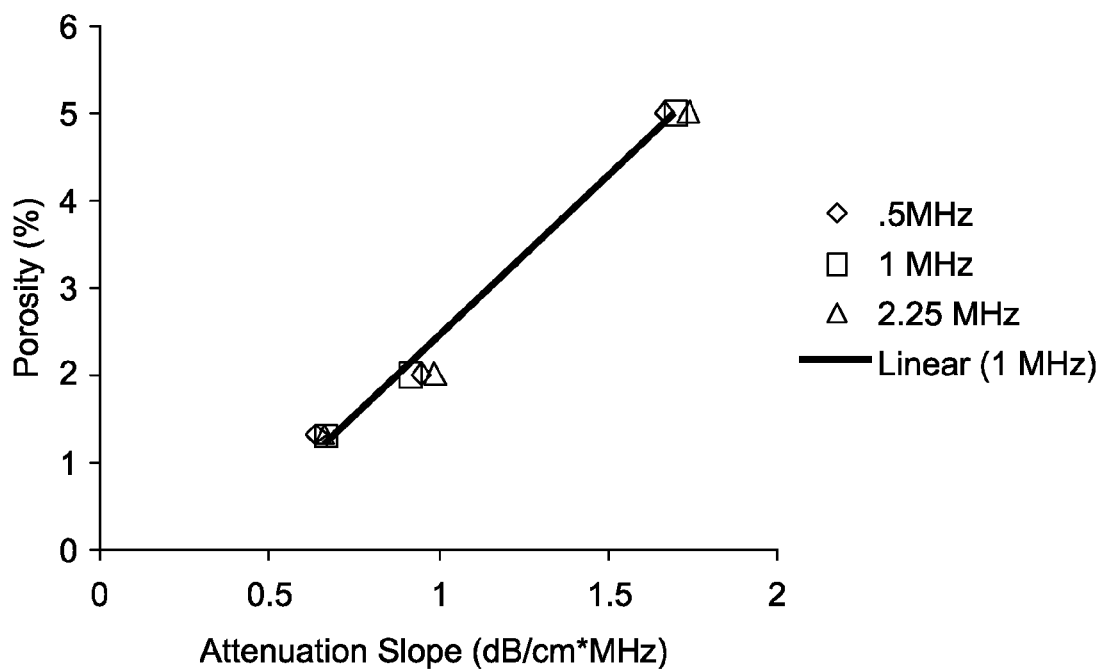
FIG. 2 is a graph plotting the porosity of three samples of known porosity as a function of the attenuation slope for the measurements plotted in FIG. 1.

Data acquired using this calibration method, such as that used to generate the plot in FIG. 1, may be used to derive a functional relationship between attenuation of ultrasonic sound waves by a composite structure, the returned frequency of ultrasonic sound waves, and porosity content of the composite structure. The measured attenuation of each composite structure is divided by the returned frequency for that measurement. This results in an attenuation slope. FIG. 2 plots porosity as a function of the attenuation slope of the measurements plotted in FIG. 1. Regression analysis may then be performed to determine a linear equation describing this relationship. The resulting equation has the form of:

$$\% \text{ porosity} = \text{Coefficient} \frac{\% * cm * MHz}{dB} * \frac{d\alpha}{df} - \text{Offset } \% \quad [1]$$

$\frac{d\alpha}{df}$ is the first order derivative of attenuation, or more simply the slope of the linear fit line describing the relationship between attenuation and returned frequency. If it is assumed that attenuation is zero at a zero MHz, $\frac{d\alpha}{df}$ is the attenuation of a sound wave divided by the returned frequency. Thus, porosity percentage may be determined with a single measurement, at a single frequency.

Coefficient is a scaling term, and

Offset is a fitting term which is equal to the porosity value for zero attenuation slope measurements.

The data described above with respect to FIGS. 1 and 2 was subjected to such a regression analysis and yielded a Coefficient value of 3.6 and an Offset value of 1.9. These constants are generally only valid for the particular ultrasonic transducer used to collect the data. The derivation of the Coefficient and the Offset will typically need to be repeated for each particular transducer to be used.

Figure 3:
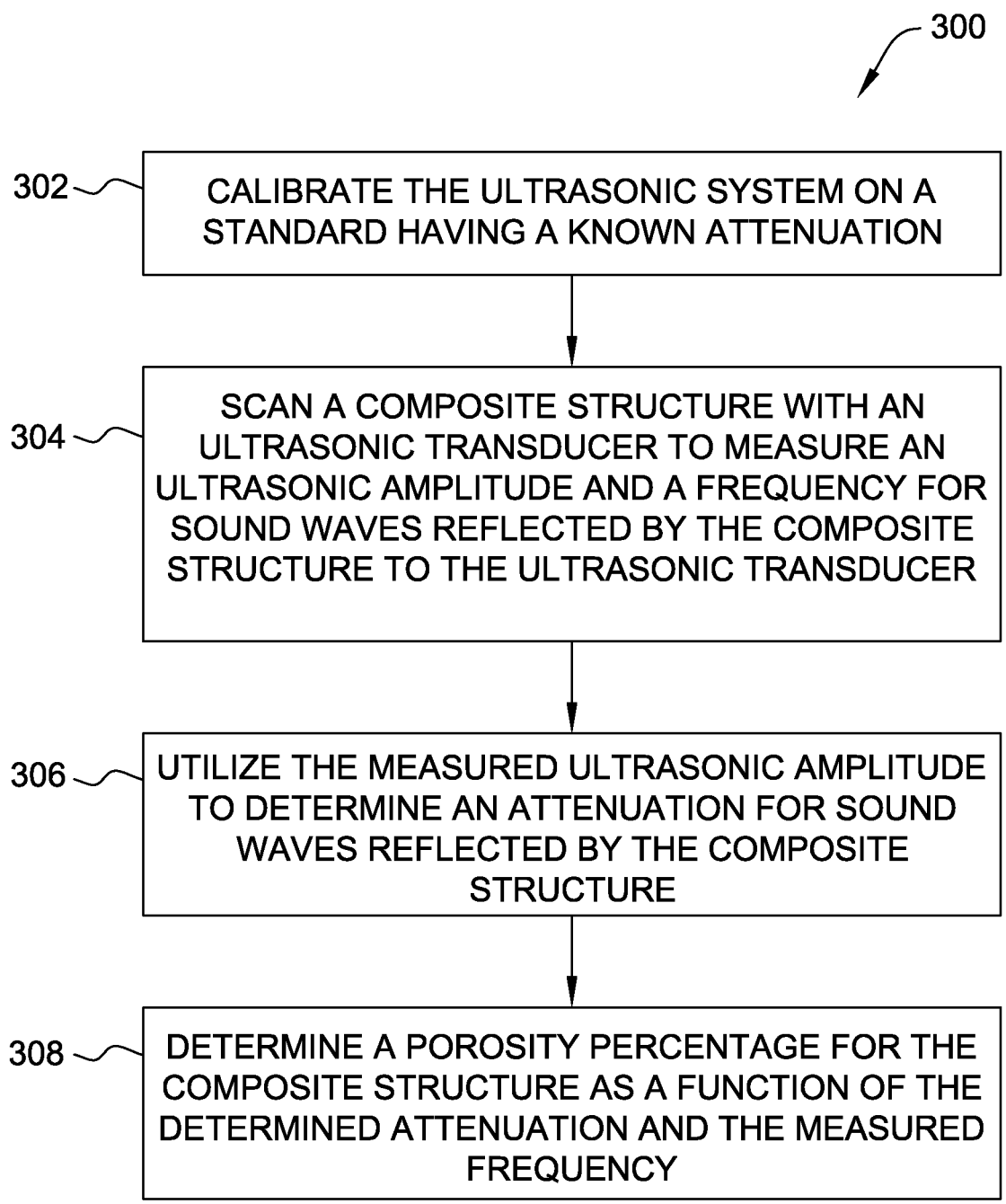
FIG. 3 is a representation of a tank-less method for non-destructively inspecting a composite structure with an ultrasonic system including an ultrasonic transducer used in some configurations of the present invention.

FIG. 3 illustrates a block diagram of a tank-less method 300 for non-destructively inspecting a composite structure with an ultrasonic system including an ultrasonic transducer. The ultrasonic system is calibrated 302 on a standard having a known attenuation. A composite structure is scanned 304 with the ultrasonic transducer to measure an ultrasonic amplitude and a frequency for sound waves reflected by the composite structure to the ultrasonic transducer. The measured ultrasonic amplitude is utilized 306 to determine an attenuation of sound waves reflected by the composite structure. The porosity percentage of the composite structure is determined 308 as a function of the determined attenuation and the measured frequency.

Figure 4:
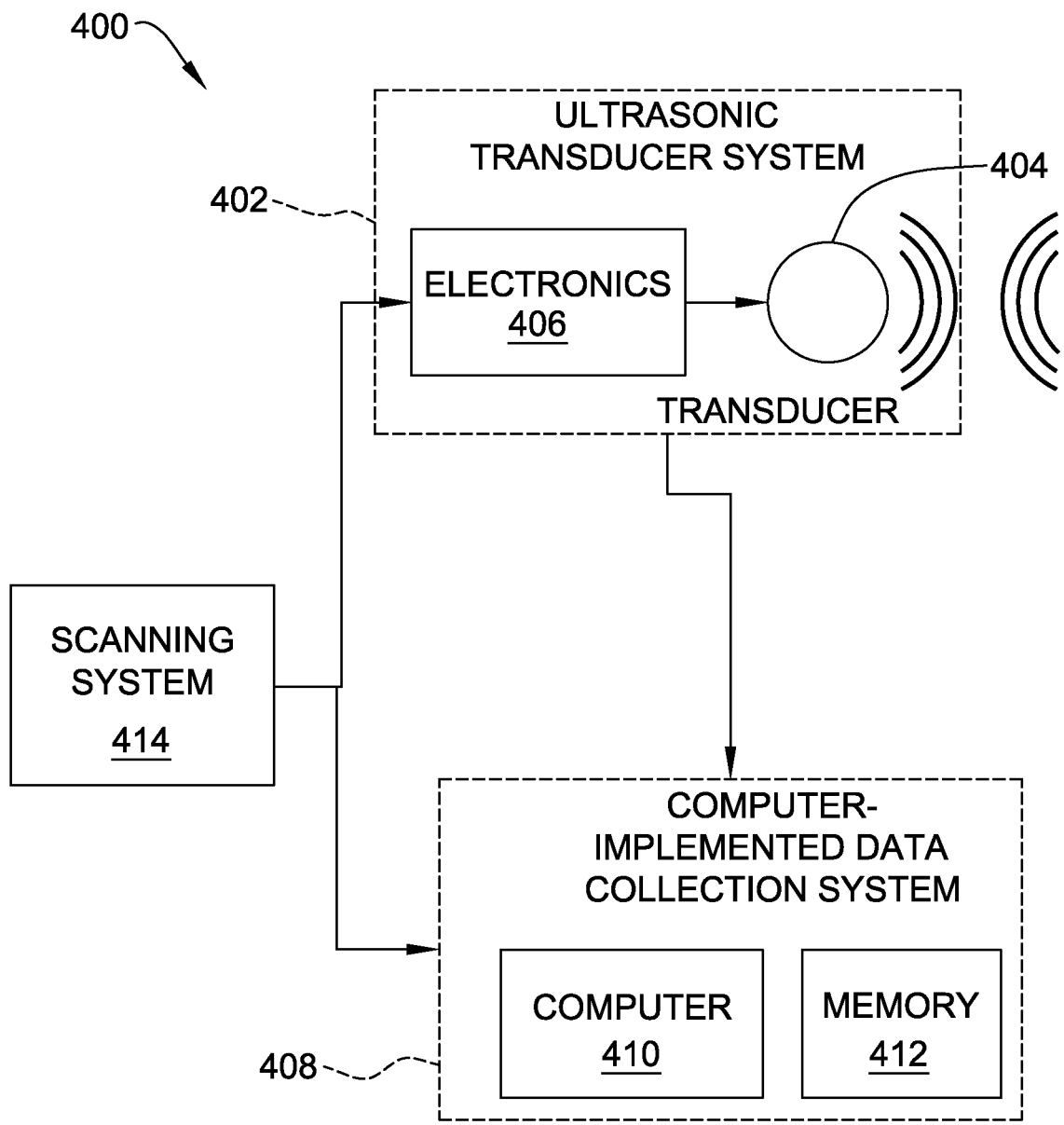
FIG. 4 is a block diagram of an inspection system including an ultrasonic transducer suitable for use with configurations of the present invention.

An example inspection system 400 suitable for performing the method 300 is illustrated in FIG. 4. System 400 includes an ultrasonic transducer system 402 having an ultrasonic transducer 404 configured to transmit and receive ultrasonic sound waves. Ultrasonic transducer system 402 includes electronic equipment 406 configured to generate and amplify the ultrasonic sound waves. System 400 includes a computer-implemented data collection system 408 having a computer 410 configured to collect ultrasonic information and memory device 412. Although illustrated separately from computer 410, memory device 412 may be a part of computer 410.

Memory device 412 is one or more devices that enable information such as executable instructions and/or other data to be stored and retrieved. Memory device 412 may include one or more computer readable media, such as, without limitation, dynamic random access memory (DRAM), static random access memory (SRAM), a solid state disk, and/or a hard disk. Memory device 412 may be configured to store, without limitation, computer-executable instructions, ultrasonic sound wave data, digital images, algorithms, scanning parameters, and/or any other type of data.

In some embodiments, ultrasonic transducer 404 generates ultrasonic sound waves at a single frequency. This single frequency may be any suitable frequency capable of sufficient penetration of the composite structure and providing a sufficient back reflection to be received by ultrasonic transducer 404. Typically, the single frequency is less than the frequency used in immersion tank environments. For example, the single frequency may be between about 500 kHz and about 2.25 MHz. In some embodiments, the single frequency is between about 500 kHz and about 1 MHz. In some embodiments, the single frequency is about 500 kHz.

In operation, a user first calibrates ultrasonic transducer system 402 using a standard of a known attenuation. The user then places ultrasonic transducer 404 adjacent a composite structure to be inspected. Electronic equipment 406 causes an ultrasonic sound wave to be transmitted toward the composite structure through ultrasonic transducer 404. The ultrasonic sound wave passes through the composite structure and is reflected off the back wall of the composite structure. Ultrasonic transducer 404 receives the back reflected sound wave. Information about the transmitted and received sound wave may be analyzed when acquired and/or may be stored in data collection system 408 for later analysis. Data collection system 408 may store raw data and/or processed data concerning the received sound waves.

System 400 measures the frequency of the reflected sound wave and utilizes the transmitted and received ultrasonic sound waves to determine the attenuation of the ultrasonic sound wave. In some embodiments, data collection system 408 measures an ultrasonic amplitude and a frequency for sound waves reflected by the composite structure. Data collection system 408 utilizes the measured ultrasonic amplitude to determine the attenuation of the sound waves reflected by the composite structure. In some embodiments, electronic equipment 406 performs one or more of the measuring and determining.

Data collection system 408 determines a porosity percentage for the composite structure as a function of the determined attenuation and the measured frequency. Specifically, formula [1] discussed above, along with the appropriately determined Coefficient and Offset, is utilized to determine the porosity percentage as a function of the determined attenuation and the measured frequency. As discussed above, if an attenuation of zero is assumed for a frequency of zero, the determined attenuation for a single measurement divided by the measured frequency is equal to $$\frac{d\alpha}{df}.$$

Thus, data collection system 408 can determine the porosity percentage by dividing the determined attenuation (in dB/cm) by the returned frequency (in MHz), substituting the result into equation [1] as $$\frac{d\alpha}{df},$$

and solving the equation.

After the porosity percentage is determined, it may be compared to a reference value. The comparison may be performed manually and/or automatically by an operator and/or data collection system 408. Thus, the determined porosity percentage may be used to determine whether or not the composite structure under inspection meets one or more standard, such as a quality control standard, defined by the reference value. A particular reference value may be applicable to an entire composite structure or only to one or more portion of the composite structure. Accordingly, a composite structure may be subject to one or more porosity threshold at one or more portion of the composite structure.

Sometimes, it may be desirable to determine the porosity percentage of a composite structure at more than one location of the composite structure. In such instances, a user may calibrate ultrasonic transducer system 402 using a standard of a known attenuation. The user then places ultrasonic transducer 404 adjacent a composite structure at a first position to be inspected. After the ultrasonic sound wave is transmitted and received, system 400 determines the porosity percentage at the first position as discussed above. The user may then move ultrasonic transducer 404 to a second position to be inspected and the process is repeated. The process may be repeated as many times as desired at as many positions as desired to determine the porosity percentage of the composite structure at the multiple positions. Information about the transmitted and received sound waves may be analyzed when acquired and/or may be stored in data collection system 408 for later analysis.

In the embodiment of FIG. 4, system 400 includes a scanning system 414. Other embodiments may not include scanning system 414. Scanning system 414 positions ultrasonic transducer 404 relative to the composite structure to be inspected. Scanning system 414 may move ultrasonic transducer 404, ultrasonic transducer system 402, or system 400, relative to a fixed composite structure to position ultrasonic transducer 404 relative to the composite structure. Alternatively, or additionally, scanning system 414 may move a composite structure relative to a fixed ultrasonic transducer 404, ultrasonic transducer system 402, or system 400 to position ultrasonic transducer 404 relative to the composite structure. The positioning of the ultrasonic transducer via scanning system 414 may be selected manually by a user or may be automatically performed according to instructions stored in data collection system 408.

Scanning system 414 permits automated scanning of a composite structure with system 400. Scanning system 414 is controlled by data collection system 408 to position ultrasonic transducer 404 at a first position relative to the composite structure to determine the porosity percentage of the composite structure at the first position. Scanning system 414 may then reposition ultrasonic transducer 404 at a second position relative to the composite structure to determine the porosity percentage of the composite structure at the second position. The process may be repeated as many times as desired at as many positions as desired to determine the porosity percentage of the composite structure at the multiple positions. Information about the transmitted and received sound waves may be analyzed when acquired and/or may be stored in data collection system 408 for later analysis. If a composite structure is large, it may be desirable to inspect the composite structure at multiple locations along its length and/or width. Inspecting the composite structure to determine the porosity percentage at many locations along the composite structure may take a significant amount of time. Accordingly, automated scanning with system 400 may save time and/or permit a user to perform other tasks while the scanning is being performed.

Figure 5:
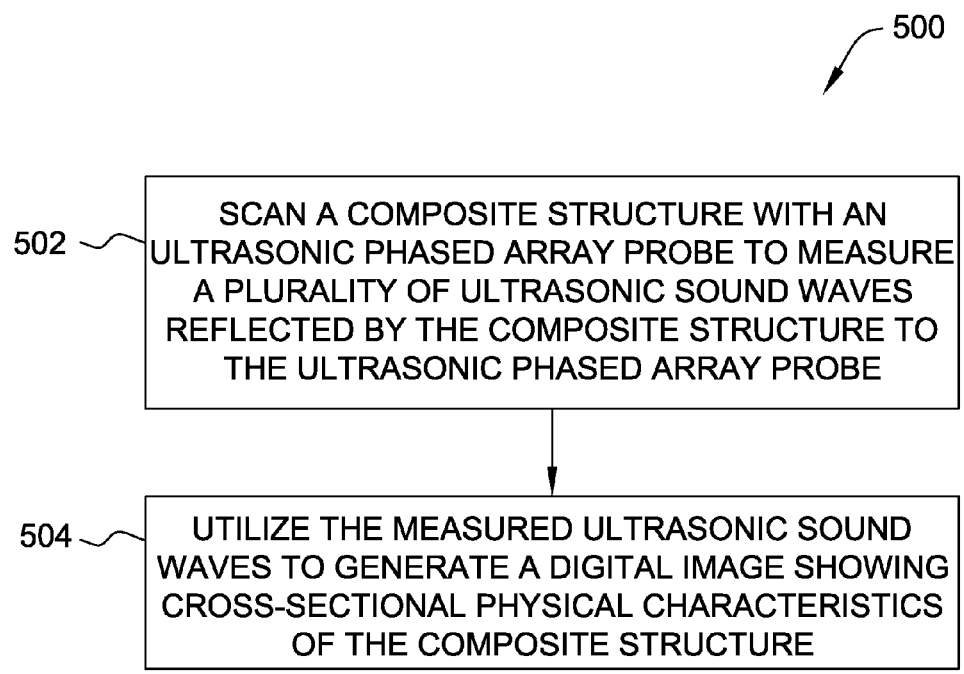
FIG. 5 is a representation of a tank-less method for non-destructively inspecting a composite structure with an ultrasonic phased array probe used in some configurations of the present invention.

In addition, or alternative, to determination of the porosity percentage of a composite structure, it is sometimes desirable to inspect a composite structure for defects, characteristics, etc. of the composite structure. As shown in FIG. 5, a tankless method 500 of inspecting a composite structure includes scanning 502 a composite structure with an ultrasonic phased array probe to measure a plurality of ultrasonic sound waves reflected by the composite structure to the ultrasonic phased array probe. The measured ultrasonic sound waves are utilized 504 to generate a digital image showing cross-sectional physical characteristics of the composite structure.

Figure 6:
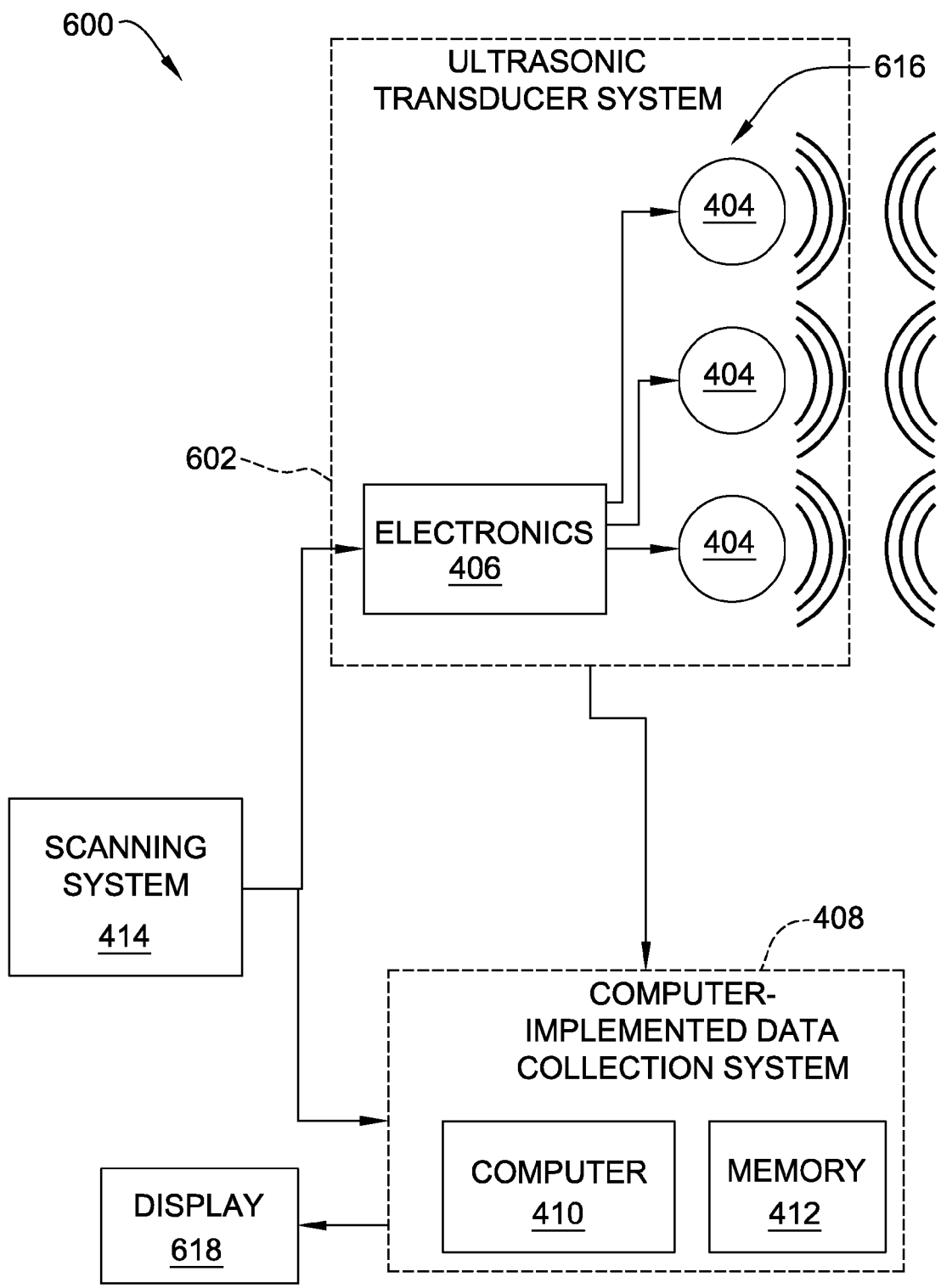
FIG. 6 is a block diagram of an inspection system including a phased array probe suitable for use with configurations of the present invention.

An example inspection system 600 suitable for performing method 500 is illustrated in FIG. 6. System 600 includes an ultrasonic transducer system 602 having an ultrasonic phased array probe 616 configured to transmit and receive ultrasonic sound waves. Ultrasonic transducer system 602 includes electronic equipment 406 configured to generate and amplify the ultrasonic sound waves. System 600 includes computer-implemented data collection system 408 having computer 410 configured to collect ultrasonic information and memory 412. System 600 includes a display device 618 for displaying an image generated by data collection system 408.

Ultrasonic phased array probe 616 includes an array of ultrasonic transducers 404. In one example embodiment, ultrasonic phased array probe 616 includes sixty-four ultrasonic transducers 404. In other embodiments, ultrasonic phased array probe 616 may include an array of more or fewer ultrasonic transducers 404. Use of ultrasonic phased array probe 616 instead of a single element probe may provide more directive energy than a single transducer probe, allowing ultrasonic phased array probe 616 to perform better with highly attenuative composite structures, such as carbon fiber composite structures.

In some embodiments, ultrasonic phased array probe 616 generates, via ultrasonic transducers 404, phase shifted ultrasonic sound waves at a single frequency. This single frequency may be any suitable frequency capable of sufficient penetration of the composite structure and providing a sufficient back reflection to be received by ultrasonic transducers 404. Typically, the single frequency is less than the frequency used in immersion tank environments. For example, the single frequency may be between about 500 kHz and about 2.25 MHz. In some embodiments, the single frequency is between about 500 kHz and about 1 MHz. More specifically, the single frequency is about 500 kHz.

System 600 includes scanning system 414, although other embodiments may not include scanning system 414. Scanning system 414 positions ultrasonic phased array probe 616 relative to the composite structure to be inspected. Scanning system 414 may move ultrasonic phased array probe 616, ultrasonic transducer system 602, or system 600, relative to a fixed composite structure to position ultrasonic phased array probe 616 relative to the composite structure. Alternatively, or additionally, scanning system 414 may move a composite structure relative to a fixed ultrasonic phased array probe 616, ultrasonic transducer system 602, or system 600 to position ultrasonic phased array probe 616 relative to the composite structure. The positioning of ultrasonic phased array probe 616 via scanning system 414 may be selected manually by a user or may be automatically performed according to instructions stored in data collection system 408.

In operation, ultrasonic phased array probe 616 is positioned by scanning system 414 at a first position adjacent a composite structure to be inspected. Electronic equipment 606 causes ultrasonic transducers 404 to transmit phase shifted sound waves toward the composite structure. The ultrasonic sound waves pass through the composite structure and are reflected off the back wall of the composite structure. The ultrasonic sound waves may be scattered (e.g., deflected, absorbed, etc.) by defects in the composite structure being inspected. Ultrasonic phased array probe 616 receives the reflected sound waves. Information about the transmitted and received sound waves may be analyzed when acquired and/or may be stored in data collection system 408 for later analysis. Data collection system 408 may store raw data and/or processed data concerning the received ultrasonic sound waves.

Figure 7:
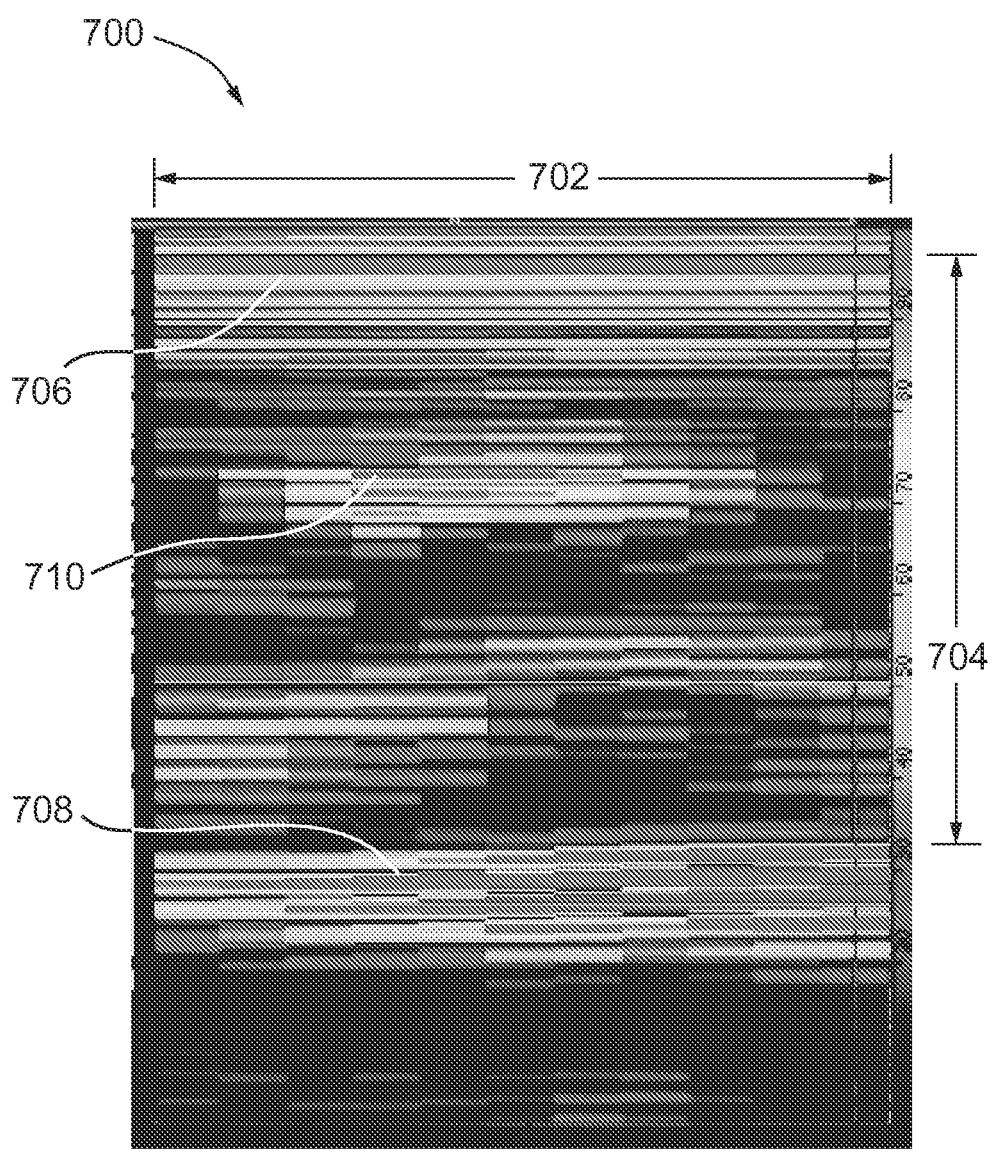
FIG. 7 is an example image showing cross sectional physical characteristics of a composite structure generated in accordance with configurations of the present invention.
Figure 8:
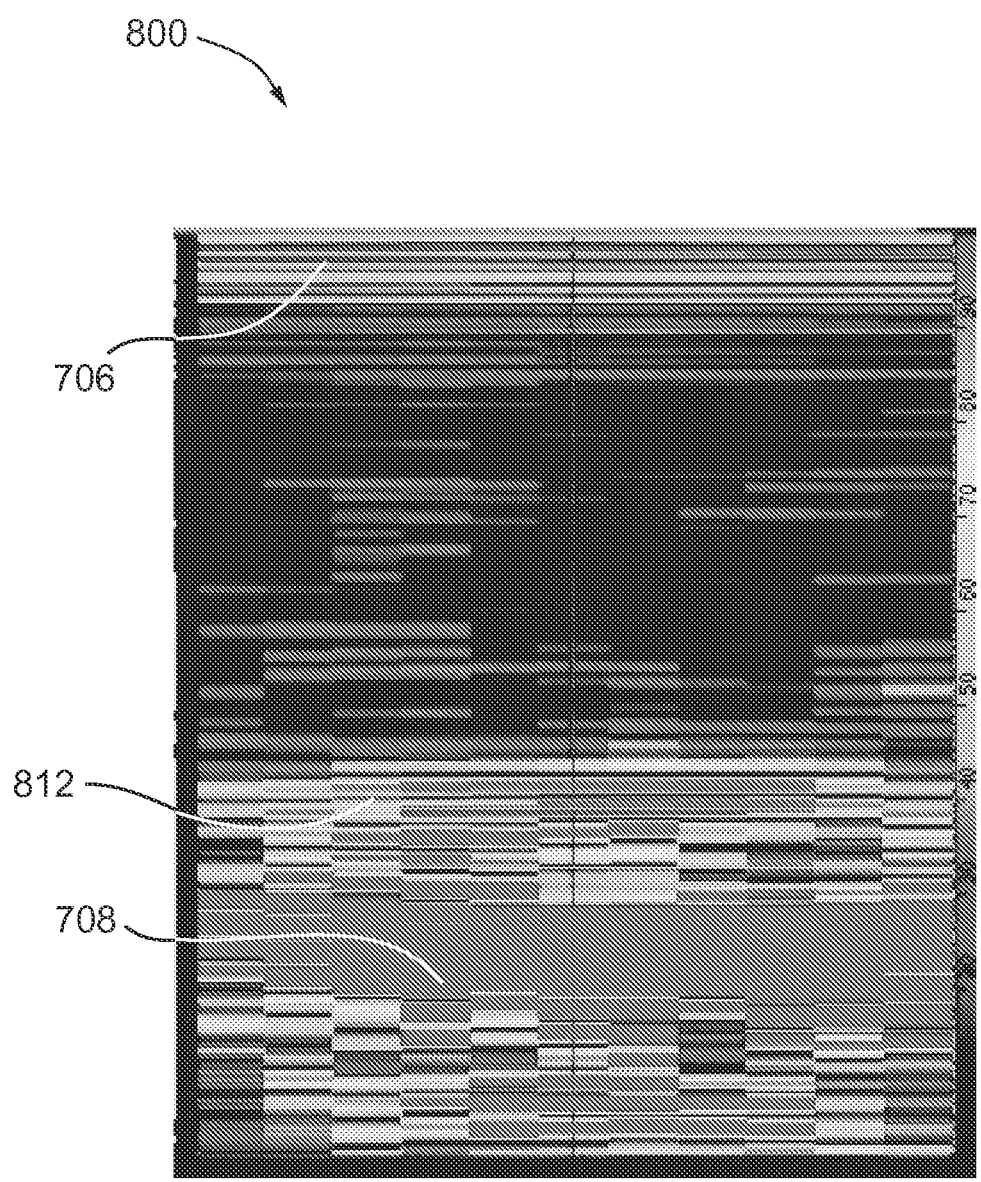
FIG. 8 is another example image showing cross sectional physical characteristics of a composite structure generated in accordance with configurations of the present invention.

The system 600 utilizes the ultrasonic sound wave data to generate a digital image showing cross sectional physical characteristics of the composite structure. In some embodiments, the digital image is displayed on a display device 618. In some embodiments, the digital image is stored by data collection system 408 for later analysis, display, etc. An example of such a digital image 700 is shown in FIG. 7. A width 702 of image 700 corresponds to the width of ultrasonic phased array probe 616. A height 704 (or thickness) of the composite structure is the distance between a front wall reflection 706 from the composite structure and a back wall reflection 708 from the composite structure. A defect 710 is visible within the composite structure. In this instance, defect 710 is a delamination, e.g. two or more plies of carbon fiber that are not bonded together. In addition to indicating the presence of defect 710, the location and approximate dimensions of defect 710 may be estimated from image 700. Further, system 600 may utilize the stored ultrasonic sound wave data to determine the position of defect 710 within the composite structure and/or the dimensions of defect 710. An example digital image 800 is shown in FIG. 8. A defect 812 is visible within the composite structure. In this instance, defect 812 is a wrinkle, e.g. two or more plies of carbon fiber that are not perfectly flat.

Scanning system 414 permits automated scanning of a composite structure with system 600. Scanning system 414 is controlled by data collection system 408 to position ultrasonic transducer array 616 at a first position relative to the composite structure to scan with ultrasonic sound waves from the ultrasonic transducer array 616. Scanning system 414 may then reposition ultrasonic transducer 404 at a second position relative to the composite structure. This process may be repeated as many times as desired, at as many positions as desired. Information about the transmitted and received sound waves may be analyzed when acquired and/or may be stored in data collection system 408 for later analysis. If a composite structure is large, it may be desirable to inspect the composite structure at multiple locations along its length and/or width. Inspecting the composite structure to determine the porosity percentage at many locations along the composite structure may take a significant amount of time. System 600 may scan a composite structure at many locations automatically to acquire ultrasonic sound wave data. A user can review the data, and/or the digital images generated from such data contemporaneously with the scan or after a scan of the entire composite structure is complete. Accordingly, automated scanning with system 600 may save time and/or permit a user to perform other tasks while the scanning is being performed.

In some embodiments, system 600 may, additionally or alternatively, be used to determine porosity percentage of a composite structure. Such embodiments may acquire ultrasonic data for determining porosity percentage while also acquiring ultrasonic data for generating digital data showing cross-sectional characteristics of a composite structure being inspected. In some such embodiments, the entire ultrasonic transducer array 616 may be used or less than all ultrasonic transducers 404 of ultrasonic transducer array 616 may be used to acquire data for determination of the porosity percentage of the composite structure being inspected. In other embodiments, such as illustrated in FIG. 9, a system 900 may include ultrasonic transducer system 402 and ultrasonic transducer system 602.

Thus, it has been shown that various configurations of the present invention provide nondestructive, tank-less methods for inspecting composite structures during the manufacturing process and that this method is advantageous for designing these components. Configurations of the present invention use only one scan for porosity determinations instead of multiple scans as was utilized for some prior art techniques. Some configurations of the present invention also use only one transducer, thereby simplifying calibration and inspection procedures. Configurations of the present invention do not utilize an immersion tank, thereby reducing costs and allowing inspection of materials too large for many existing immersion tanks. Method configurations of the present invention are relatively simple and straightforward and utilize skills that most ultrasonic inspectors possess.

Some embodiments described herein involve the use of one or more computers or computing devices. Such devices typically include a processor or controller, such as a general purpose central processing unit (CPU), a graphics processing unit (GPU), a microcontroller, a reduced instruction set computer (RISC) processor, an application specific integrated circuit (ASIC), a programmable logic circuit (PLC), and/or any other circuit or processor capable of executing the functions described herein. The methods described herein may be encoded as executable instructions embodied in a computer readable medium, including, without limitation, a storage device and/or a memory device. Such instructions, when executed by a processor, cause the processor to perform at least a portion of the methods described herein. The above examples are exemplary only, and thus are not intended to limit in any way the definition and/or meaning of the term processor.

While the invention has been described in terms of various specific embodiments, those skilled in the art will recognize that the invention can be practiced with modification within the spirit and scope of the claims.

What is claimed is:

1. A method for non-destructively inspecting a composite structure with an ultrasonic system including an ultrasonic probe, said method comprising:
   calibrating the ultrasonic system on a standard;
   positioning the composite structure in a tank-less environment;
   scanning the composite structure with an ultrasonic phased array probe of the ultrasonic system to measure ultrasonic sound waves reflected by the composite structure to the ultrasonic phased array probe;
   determining a physical characteristic of the composite structure based at least in part on the measured ultrasonic sound waves to generate a digital image showing cross-sectional physical characteristics of the composite structure; and,
   utilizing the measured ultrasonic sound waves to determine an attenuation for sound waves reflected by the composite structure; and,
   wherein:
      said scanning the composite structure comprises scanning the composite structure with the ultrasonic system to measure an ultrasonic amplitude and a frequency for sound waves reflected by the composite structure to the ultrasonic phased array probe; and,
      said determining a physical characteristic comprises determining a porosity percentage for the composite structure as a function of the determined attenuation and the measured frequency of the ultrasonic sound waves reflected by the composite structure.

2. A method in accordance with Claim 1, wherein the sound waves reflected by the composite structure comprise a back reflection from the composite structure.

3. A method in accordance with Claim 1, wherein said scanning the composite structure comprises scanning the composite structure using a single frequency of sound waves emitted by the ultrasonic probe.

4. A method in accordance with claim 3, wherein the single frequency is less than about 2 MHz.

5. A method in accordance with Claim 1, wherein said determining the porosity percentage for the composite structure comprises a linear equation.

6. A method in accordance with Claim 1, wherein said scanning a composite structure comprises scanning the composite structure with an ultrasonic phased array probe at a frequency of less than about 2 MHz.

7. An apparatus for non-destructively inspecting a composite structure, said apparatus comprising:
   an ultrasonic system including:
      an ultrasonic phased array probe configured to transmit and receive ultrasonic sound waves in a tankless environment; and,
      electronic equipment configured to operate the ultrasonic phased array probe to generate and amplify ultrasonic sound waves; and,
   a data collection system including a computer, said data collection system configured to collect ultrasonic information;
   said apparatus configured to:
      scan the composite structure with the ultrasonic system to measure ultrasonic amplitude and a frequency of ultrasonic sound waves reflected by the composite structure to the ultrasonic phased array probe; and,
      determine a porosity percentage of the composite structure based at least in part on the measured ultrasonic sound waves to generate a digital image showing cross-sectional physical characteristics of the composite structure.

8. An apparatus in accordance with claim 7, wherein the apparatus is configured to calibrate the ultrasonic system on a standard, and utilize the measured ultrasonic sound waves to determine attenuation for sound waves reflected by the composite structure, and wherein
   said apparatus is configured to determine the porosity percentage as a function of the determined attenuation and the measured frequency of the ultrasonic sound waves reflected by the composite structure.

9. An apparatus in accordance with claim 8, wherein said apparatus is configured to measure the ultrasonic amplitude and the frequency of sound waves comprising a back reflection from the composite structure.

10. An apparatus in accordance with claim 8, wherein the ultrasonic phased array probe emits a single frequency of sound waves.

11. An apparatus in accordance with claim 10, wherein the single frequency is less than about 2 MHz.

12. An apparatus in accordance with claim 8, wherein said apparatus is configured to determine the porosity percentage for the composite structure as a function of the determined attenuation and the measured frequency utilizing a linear equation.

13. An apparatus in accordance with claim 8, further comprising a scanning system configured to position the ultrasonic phased array probe relative to the composite structure to obtain ultrasonic information.

14. An apparatus in accordance with Claim 7, further comprising a scanning system configured to position said ultrasonic phased array probe relative to the composite structure to obtain ultrasonic information.

15. An apparatus in accordance with claim 14, wherein said apparatus is configured to:
   scan the composite structure with the ultrasonic phased array probe at a plurality of locations of the composite structure to measure a plurality of ultrasonic sound waves reflected by the composite structure to the ultrasonic phased array probe; and,
   utilize the measured ultrasonic sound waves to generate a plurality of digital images, each of the plurality of digital images showing cross-sectional physical characteristics of a different one of the plurality of locations of the composite structure.

\* \* \* \* \*